US008481040B2

(12) United States Patent
Rummel et al.

(10) Patent No.: US 8,481,040 B2
(45) Date of Patent: Jul. 9, 2013

(54) CARRIER FOR TARGETING NERVE CELLS (75) Inventors: Andreas Rummel, Hannover (DE);
Tanja Weil, Frankfurt am Main (DE);
Aleksandrs Gutcaits, Riga (LV)

(73) Assignee: Syntaxin Limited, Abingdon, Oxfordshire (GB)

( * ) Notice: Subject to any disclaimer, the term of this patent is extended or adjusted under 35 U.S.C. 154(b) by 754 days.

(21) Appl. No.: 11/919,302

(22) PCT Filed: Apr. 26, 2006

(86) PCT No.: PCT/EP2006/003896
§ 371 (c)(1),
(2), (4) Date: Feb. 29, 2008

(87) PCT Pub. No.: WO2006/114308
PCT Pub. Date: Nov. 2, 2006

(65) Prior Publication Data
US 2009/0311275 A1    Dec. 17, 2009

(30) Foreign Application Priority Data
Apr. 26, 2005  (DE) .................. 10 2005 019 302

(51) Int. Cl.
C07K 14/33  (2006.01)
(52) U.S. Cl.
USPC ....................... 424/179.1; 424/94.3
(58) Field of Classification Search
None
See application file for complete search history.

(56) References Cited

U.S. PATENT DOCUMENTS

2003/0215468 A1    11/2003  Williams et al.
2007/0258992 A1 *  11/2007  Atassi ................ 424/190.1

FOREIGN PATENT DOCUMENTS

AU    2005/281830    *  3/2006
DE    10 2004 043009.8    9/2004

OTHER PUBLICATIONS

Rummel et al (Molecular Microbiology, 2002, 51(3), p. 631-643).*
Bowie et al (Science, 1990, 247:1306-1310).*
Greenspan et al. (Nature Biotechnology 7: 936-937, 1999).*
Rummel et al (Molecular Microbiology, 2004,51(3), 631-643).*
Rummel, Andreas et al, PNAS, Jan. 2, 2007, vol. 104(1), pp. 359-364, Identification of the protein receptor binding site of botulinum neurotoxins B and G proves the double-receptor concept.*
Binz, T., et al., "Arg$^{362}$ and Tyr$^{365}$ of the Botulinum Neurotoxin Type A Light Chain Are Involved in Transition State Stabilization," Biochemistry, 41:1717-1723 (2002).
Gimenez, J.A. and DasGupta, B.R., "Botulinum Type A Neurotoxin Digested with Pepsin Yields 132, 97, 72, 45, 42, and 18 kD Fragments," J. of Protein Chemistry, 12(3): 351-363 (1993).

(Continued)

Primary Examiner — Albert Navarro
Assistant Examiner — Ginny Portner
(74) Attorney, Agent, or Firm — McCarter & English, LLP; Steven G. Davis; Jin Wang, Esq.

(57) ABSTRACT

The present invention relates to a transport protein which can be obtained by modifying the heavy chain of the neurotoxin formed by *Clostridium botulinum* wherein (i) the protein binds specifically to nerve cells with a higher or lower affinity as the native neurotoxin; (ii) the protein has an increased or reduced neurotoxicity compared to the native neurotoxin, the neurotoxicity being preferably determined in the hemidiaphragma assay; and/or (iii) the protein comprises a lower affinity against neutralizing antibodies compared to the native neurotoxin. The invention also relates to methods for producing the same and the use thereof in cosmetic and pharmaceutical compositions.

21 Claims, 6 Drawing Sheets

OTHER PUBLICATIONS

Göschel, H., et al., "Botulinum A Toxin Therapy: Neutralizing and Nonneutralizing Antibodies-Therapeutic Consequences," *Exp. Neurol.*, 147:96-102 (1997).

Habermann, E., et al., "Tetanus Toxin Blocks the Neuromuscular Transmission in vitro Like Botulinum A Toxin," *Naunyn-Schmiedeberg's Arch. Pharmacol.*, 311:33-40 (1980).

Herreros, J., et al., "C-terminal Half of Tetanus Toxin Fragment C is Sufficient for Neuronal Binding and Ineraction with a Putative Protein Receptor," *Biochem. J.*, 347:199-204 (2000).

Hutson, R.A., et al., "Nucleotide Sequence of the Gene Coding for Non-Proteolytic *Clostridium botulinum* Type B Neurotoxin: Comparison with Other Clostridial Neurotoxins," *Current Microbiology*, 28: 101-110 (1994).

Lacy, D.B., et al., "Crystal Structure of Botulinum Neurotoxin Type A and Implications for Toxicity," *Nature Structural Biology*, 5(10): 898-902 (1998).

Rummel, A., et al., "Synaptotagmins I and II Act as Nerve Cell Receptors for Botulinum Neurotoxin G," *J. of Biol. Chem.*, 279(29):30865-30870 (2004).

Rummel, A., et al., "The $H_{cc}$-domain of Botulinum Neurotoxins A and B Exhibits a Singular Ganglioside Binding Site Displaying Serotype Specific Carbohydrate Interaction," *Molecular Microbiology*, 51(3): 631-643 (2004).

Santos-Buelga, J.A., et al., "Characterization of the Genes Encoding the Botulinum Neurotoxin Complex in a Strain of *Clostridium botulinum* Producing Type B and F Neurotoxins," *Current Microbiology*, 37:312-318 (1998).

Shone, C.C., et al., "Inactivation of *Clostridium botulinum* Type A Neurotoxin by Trypsin and Purification of Two Tryptic Fragments," *Eur. J. Biochem.*, 151:75-82 (1985).

Smith, T.J., et al., "Sequence Variation Within Botulinum Neurotoxin Serotypes Impacts Antibody Binding and Neutralization," *Infection and Immunity*, 73(9):5450-5457 (2005).

Sycha, T., et al., "Botulinum Toxin in the Treatment of Rare Head and Neck Pain Syndromes: A Systematic Review of the Literature," *J. Neurol.*, 251(1):Jan. 19-30, 2004.

Willems, A., et al., "Sequence of the Gene Coding for the Neurotoxin of *Clostridium botulinum* Type A Associated with Infant Botulism: Comparison with other Clostridial Neurotoxins," *Res. Microbiol.*, 144:547-556 (1993).

Maksymowych, A.B. and Simpson, L.L., "Structural Features of the Botulinum Neurotoxin Molecule that Govern Binding andTranscytosis Across Polarized Human Intestinal Epithelial Cells," *J. Pharmacol. and Exp. Therapeutics*, 310(2):633-641 (May 12, 2004).

\* cited by examiner

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: cleavage site
<220> FEATURE:
<221> NAME/KEY: VARIANT
<222> LOCATION: 2, 3, 4, 18, 19
<223> OTHER INFORMATION: Xaa = any naturally occuring amino acid
<220> FEATURE:
<221> NAME/KEY: VARIANT
<222> LOCATION: 5, 17
<223> OTHER INFORMATION: Xaa = a selection from Alanine, Valine, Serine,
```

```
              Threonine and Glycine

<400> SEQUENCE: 1

Cys Xaa Xaa Xaa Xaa Lys Thr Lys Ser Leu Val Pro Arg Gly Ser Lys
 1               5                  10                  15

Xaa Xaa Xaa Cys
            20
```

CARRIER FOR TARGETING NERVE CELLS

RELATED APPLICATIONS

This application is the U.S. National Stage of International Application No. PCT/EP2006/003896, filed on Apr. 26, 2006, published in German, and claims priority under 35 U.S.C. §119 or 365 to German Application No. 10 2005 019 302.1, filed on Apr. 26, 2005.

SEQUENCE LISTING

The instant application contains a Sequence Listing which has been submitted in ANSI format via EFS-Web and is hereby incorporated by reference in its entirety. Said ANSI copy, created on Mar. 18, 2011, is named 0981130103__1.txt and is 840 bytes in size.

The present invention relates to a transport protein which binds to neurons with a higher or lower affinity than the neurotoxin formed by *Clostridium botulinum*. The transport protein is preferably absorbed by receptor-mediated endocytosis. This protein is used as a transporting means translocating other chemical substances (e.g. proteases) from the acid endosomal compartment into the cytosol of neurons which are unable physiologically to penetrate into the cytosol of nerve cells through the plasma membrane. The present invention relates, in particular, to the use of a transport protein for the introduction of inhibitors of the release of neurotransmitters.

Nerve cells release transmitter substances by exocytosis. The fusion of the membranes of intracellular vesicles with the plasma membrane is referred to as exocytosis. In the course of this process the vesicular contents is simultaneously released into the synaptic gap. The fusion of the two membranes is regulated by calcium, reacting with the protein synaptotagmin. Jointly with other co-factors synaptotagmin controls the status of three so-called fusion proteins, SNAP-25, synaptobrevin 2 and syntaxin 1A. While syntaxin 1A and synaptobrevin 2 are integrated into the plasma and/or vesicle membrane, SNAP-25 binds only lightly to the plasma membrane. To the extent that the intracellular calcium concentration increases, the three proteins bind to one another, both membranes approaching one another and subsequently fusing together. In the case of cholinergic neurons acetyl choline is released, causing muscle contractions, perspiration and other cholinergically provoked reactions.

The above mentioned fusion proteins are the target molecules (substrates) of the light chain (LC) of the clostridial neurotoxins, formed by the bacteria *C. botulinum, C. butyricum, C. baratii* and *C. tetani*.

The anaerobic, gram-positive bacterium *C. botulinum* produces seven different serotypes of the clostridial neurotoxins. The latter are referred to as the Botulinus neurotoxins (BoNT/A to BoNT/G). Among these, in particular BoNT/A and BoNT/B cause a neuroparalytic disorder in humans and animals, referred to as botulism. The spores of *C. botulinum* can be found in the soil, but may also develop in incorrectly sterilised and sealed home-made food preserves, to which many cases of botulism are attributed.

BoNT/A is the most active of all known biological substances. As little as 5-6 pg of purified BoNT/A represents an MLD (Multiple Lethal Dose). One unit (Engl.: Unit, U) of BoNT/A is defined as the MLD, killing half of the female Swiss Webster mice, each weighing 18-20 g, after intraperitoneal injection. Seven immunologically different BoNTs were characterised. They are denoted as BoNT/A, B, C1, D, E, F and G and may be distinguished by neutralisation with serotype-specific antibodies. The different serotypes of BoNTs differ in affected animal species with regard to severity and duration of the paralysis caused. Thus, with regard to paralysis, BoNT/A is 500 times more potent in rats for example, than BoNT/B. In addition, BoNT/B has proved to be non-toxic in primates at a dosage of 480 U/kg of body weight. The same quantity of BoNT/A corresponds to 12 times the lethal dose of this substance in primates. On the other hand, the duration of paralysis after BoNT/A injection in mice is ten times longer than after injection of BoNT/E.

BoNTs are used for treating neuromuscular disorders, characterised by hyperactivity in skeleton muscles, caused by pathologically overactive peripheral nerves. BoNT/A has been approved by the U.S. Food and Drug Administration for treating blepharospasm, strabism, hyperhidrosis, wrinkles and hemi-facial spasms. Compared to BoNT/A the remaining BoNT serotypes are evidently less efficacious and manifest a shorter duration of efficacy. Clinical effects of BoNT/A administered peripheral-intramuscularly are usually noticeable within a week. The duration of symptom suppression by one single intramuscular injection of BoNT/A is normally about three to six months.

The clostridial neurotoxins specifically hydrolyse different proteins of the fusion apparatus. BoNT/A, C1 and E break up SNAP-25, while BoNT/B, D, F, G as well as tetanus neurotoxin (TeNT) attack the vesicle-associated membrane protein (VAMP) 2—also referred to as synaptobrevin 2—. BoNT/C1 furthermore breaks up syntaxin 1A.

The *Clostridium* bacteria release the neurotoxins as single-chain polypeptides each having 1251 to 1315 amino acids. Thereafter endogenous proteases split each of these proteins at a defined location into 2 chains each ('nicking'), the two chains however remaining interlinked by a disulphide-bridge. These dual-chain proteins are referred to as holotoxins (see Shone et al. (1985), Eur. J. Biochem. 151, 75-82). The two chains have different functions. While the smaller fragment, the light chain (light chain=LC), represents a $Zn^{2+}$-dependent endoprotease, the larger unit (heavy chain=HC) represents the transporting means of the light chain. By treating the HC with endopeptidases two 50 kDa fragments were brought about (see Gimenez et al. (1993), J. Protein Chem. 12, 351-363). The amino-terminal half ($H_N$-fragment) integrates into membranes at a low pH-value and translocates the LC into the cytosol of the nerve cell. The carboxyl-terminal half ($H_C$-fragment) binds to complex polysialogangliosides, occurring exclusively in nerve cell membranes and to protein receptors identified only partially to date (Halpern et al. (1993), Curr Top Microbial Immunol 195, 221-241). The latter explains the high neuroselectivity of the clostridial neurotoxins. Crystalline structures confirm that BoNT/A disposes of three domains, which may be harmonised by the three steps of the action mechanism (see Lacy et al. (1998), Nat. Struct. Biol. 5, 898-902). Moreover, these data give rise to the conclusion that within the $H_C$-fragment two autonomous subunits (sub-domains) exist of 25 kDa each. The first proof for the existence of the two functional sub-domains was brought about by the amino-terminal ($H_{CN}$) and the carboxyl-terminal half ($H_{CC}$) of the $H_C$-fragment of the TeNT, which were expressed in recombinant form and which revealed that the $H_{CC}$-, but not the $H_{CN}$ domain binds to neurons (see Herreros et al. (2000), Biochem. J. 347, 199-204). At a later stage, a single ganglioside binding site within the $H_{CC}$-domains of BoNT/A and B was localised and characterised (see Rummel et al. (2004), Mol. Microbiol. 51, 631-643). The site for binding the synaptotagmin I and II, identified as protein receptor for BoNT/B and G, could likewise be restricted to the region of the $H_{CC}$-domains of BoNT/B and G (see Rummel et al.

(2004), J Biol Chem 279, 30865-70). The document does, however, not disclose the amino acids relevant to the binding pocket of BoNT/B and G.

Under physiological conditions the HC with the $H_C$-fragment binds to neuronal gangliosides, is absorbed inside the cell by receptor-mediated endocytosis and reaches the natural vesicle circulation via the endosomal compartment. In the acid medium of the early endosomes, the $H_N$ fragment penetrates into the vesicle membrane and forms a pore. Each substance (X), linked to the HC via a disulphide bridge, will be split off the HC by intracellular redox systems, gaining access to the disulphide bridge and reducing it. X will ultimately appear in the cytosol.

In the case of the clostridial neurotoxins the HC is the carrier of an LC, splitting its specific substrate in the cytosol in the final step. The cycle of complex formation and dissociation of the fusion proteins is interrupted and the release of acetyl choline is consequently inhibited. As a result thereof, striated muscles are paralysed and sweat glands cease their secretion. The active period of the individual BoNT serotypes differs and depends on the presence of intact LC in the cytosol. As all neurons possess receptors for clostridial neurotoxins, it is not only the release of acetyl choline which may be affected, but potentially also the release of the substance P, of noradrenalin, GABA, glycine, endorphin and other transmitters and hormones.

That the cholinergic transmission is blocked preferentially, may be explained by the fact that the HC in the periphery enters into the neuron. Central synapses are protected by the blood-brain-barrier, which cannot be surmounted by proteins.

In a ligand-receptor study specific amino acid residues were substituted within the $H_{CC}$-domain of BoNT/B and G in order to identify and characterise the binding pocket of the protein receptor in order to thus modify the affinity to the protein receptor. The affinity of the mutated $H_C$-fragments of BoNT/B and G were determined by synaptotagmin in gluthathione-5-transferase-(GST)-pull-down experiments. The HC exhibiting the same mutations was subsequently coupled to LC-B or, respectively LC-G. The potency of these constructs was analysed by means of the isolated nerve-muscle-preparation of the mouse (Hemi-Diaphragm-Assay=HDA). In this preparation the Nervus phrenicus is to be found, which consists of cholinergic motor neurons and represents the most important physiological object of clostridial neurotoxins. Subsequently, individual amino acids were substituted in the $H_{CC}$-domain of BoNT/A in a depression, located analogously to the site of the protein-receptor-binding pockets in BoNT/B and G. The full-length BoNT/A single mutants were subsequently likewise analysed by HDA with regard to modified potency, giving indications as to modified ligand-protein-receptor-interactions.

In the more recent past, the BoNT/A complex, also referred to as progenitor toxin A, has been used for treating motor dystonias, as well as for attenuating excessive sympathetic activity (see Benecke et al. (1995), Akt. Neurol. 22, 209ff) and for alleviating pain and migraine (see Sycha et al. (2004), J. Neurol. 251, 19-30). This complex consists of the neurotoxin, various haemagglutinines and a non-toxic, non-haemagglutinating protein. The complex dissociates within a few minutes at physiological pH. The resultant neurotoxin is the sole ingredient of the complex which is therapeutically relevant and brings about an alleviation of the symptoms. Since the underlying neurological illness is not cured, the complex needs to be injected again at intervals of three to four months. Depending on the quantity of the injected foreign protein, some patients develop specific BoNT/A-antibodies. These patients become resistant to the neurotoxin. Once antigen-sensitive cells have recognised the neurotoxin and antibodies have been formed, the relevant memory cells are conserved over years. For this reason it is important to treat the patients with preparations of the highest possible activity at the lowest possible dosage. The preparations should furthermore not contain any further proteins of bacterial origin, since these may act as immuno-adjuvants. Such substances attract macrophages, which recognise both the immuno-adjuvants as well as the neurotoxins, presenting them to the lymphocytes, which thereupon respond by forming immunoglobulins. Consequently, only products of extreme purity, not containing any foreign proteins, should be used for therapy. The resistance of patients to the neurotoxin, viewed at a molecular level, is based predominantly on the presence of neutralising antibodies.

In what follows, the present invention proposes a transport protein (Trapo), which is able to overcome the above described problems of the methods known to date.

This object was obtained by a new transport protein, which can be obtained by modifying the heavy chain of the neurotoxin formed by *Clostridium botulinum*, wherein (i) the protein binds to nerve cells with a higher or lower affinity than the native neurotoxin;

(ii) the protein has an increased or reduced neurotoxicity compared to the native neurotoxin, the neurotoxicity being preferably determined in the hemidiaphragm assay; and/or, (iii) compared to the native neurotoxin, the protein exhibits a lower affinity in relation to neutralising antibodies.

According to a preferred embodiment of the present invention, a transport protein is provided which binds to nerve cells with a higher or lower affinity than the native neurotoxin formed by *C. botulinum*.

According to a further preferred embodiment of the present invention, a transport protein is provided which is obtained by modifying the HC of the neurotoxin formed by *C. botulinum*, the protein binding specifically to nerve cells with a higher or lower affinity than the native neurotoxin. The transport protein is preferably absorbed by these cells by endocytosis.

In addition, according to a further preferred embodiment, a transport protein is provided which is obtained by modifying the HC of the neurotoxin formed by *C. botulinum*, the protein, by substituting surface-exposed amino acids, in particular on the ganglioside- and protein-receptor binding pockets of the binding of neutralising antibodies no longer being accessible.

In what follows, terms are defined, which are to be understood in the context of the present application.

"Binding to nerve cells with a higher or lower affinity than native neurotoxin". The native neurotoxin is in this case the native neurotoxin of *C. botulinum*. Preferably, the native neurotoxin is in this context Botulinus neurotoxin A and/or Botulinus neurotoxin B and/or Botulinus neurotoxin G from *C. botulinum*. The Botulinus neurotoxin prepared in recombinant form from E. coli, which, inter alia, contains the amino acid sequence identical to the native Botulinus neurotoxin, acts in a pharmacologically identical manner to the native Botulinus neurotoxin and is referred to as recombinant Botulinus neurotoxin wild type. The nerve cells mentioned in this case are cholinergic motor neurons. Preferably, the transport protein binds specifically to the molecules associated with the plasma membrane, transmembrane proteins, synaptic vesicle proteins, a protein of the synaptotagmin family or the synaptic vesicle glycoproteins 2 (SV2), preferably synaptotagmin I and/or synaptotagmin II and/or SV2A, SV2B or SV2C, particularly preferably human synaptotagmin I and/or human synaptotagmin II and/or human SV2A, SV2B or SV2C.

Bonding is preferably determined in vitro. Particularly preferably, the determination is performed by using a GST-pull-down-assay, elucidated in detail in the examples.

"the protein has an increased or reduced neurotoxicity compared to the native neurotoxin". The native neurotoxin is in this case the native neurotoxin of C. botulinum. Preferably, the native neurotoxin is in this context the Botulinus neurotoxin A and/or Botulinus neurotoxin B and/or Botulinus neurotoxin G from C. botulinum. The Botulinus neurotoxin prepared in recombinant form from E. coli, which, inter alia, contains the amino acid sequence identical to the native Botulinus neurotoxin, acts in a pharmacologically identical manner to the native Botulinus neurotoxin and is referred to as recombinant Botulinus neurotoxin wild type. The nerve cells mentioned in this case are cholinergic motor neurons. The neurotoxicity is preferably determined with the aid of the Hemi-Diaphragm-Assay (HDA) known in the art. The neurotoxicity of the mutants can preferably be determined as described by Habermann et al., Naunyn Schmiedeberg's Arch. Pharmacol. 311 (1980), 33-40.

"Neutralising antibodies". Neutralising antibodies directed against Botulinus neurotoxin are known (Göschel H, Wohlfarth K, Frevert J, Dengler R, Bigalke H. Botulinum A toxin therapy: neutralizing and nonneutralizing antibodies—therapeutic consequences, Exp. Neurol. 1997 September; 147(1):96-102). It was found that antibodies neutralising neurotoxin interact, in particular, with the active centres such as, for example, the ganglioside- and protein-receptor binding pockets within the $H_{CC}$-domain of the neurotoxin. If the surfaces surrounding the binding pockets are modified in the neurotoxin by amino acid substitutions without negatively impairing their functionality, the neutralising antibodies lose their binding sites and the mutated neurotoxin is no longer neutralised.

The term "modification of the heavy chain of the neurotoxin formed by C. botulinum." The amino acid and/or nucleic acid sequence of the heavy chain (HC) of the neurotoxin formed by C. botulinum are generally available from publicly accessible databases, for each of the known serotypes A to G (also refer to table 1). Modification includes in this context that at least one amino acid is deleted, added, inserted into the amino acid sequence, or that at least one amino acid of the native neurotoxin is substituted by another naturally occurring or not naturally occurring amino acid and/or that one amino acid in the given amino acid sequence is modified post-translationally. Post-translational modifications include in this context glycosylations, acetylations, acylations, de-aminations, phosphorylisations, isoprenylisations, glycosyl phosphatidyl inositolisations and further modifications known to the person skilled in the art.

The HC of the neurotoxin formed by C. botulinum includes three sub-domains, i.e. the amino-terminal 50 kDa-sized translocation domain $H_N$, the 25 kDa $H_{CN}$-domain following thereon, and the carboxyl-terminally situated 25 kDa $H_{CC}$-domain. Together, the $H_{CN}$- and $H_{CC}$-domains are denoted as $H_C$-fragment. The corresponding amino acid sections of the respective sub-domains for the individual serotypes and their variations are apparent from Table 1.

"Ganglioside Receptor"

The HCs of the Botulinus neurotoxins exhibit a high affinity to peripheral nerve cells which is mediated predominantly by the interaction with complex polysialogangliosides—these are glycolipids consisting of more than one sialic acid—(Halpern et al. (1995), Curr. Top. Microbiol. Immunol. 195, 221-41; WO 2006/02707). The LCs bound to them consequently only reach this cell type and become active in these cells only. BoNT/A and B merely bind one ganglioside GT1b molecule.

In the case of BoNT/B and BoNT/G the protein receptors are synaptotagmin I and synaptotagmin II. In the case of BoNT/A the protein receptors are the synaptic vesicles glycoproteins 2 (SV2), preferably SV2A, SV2B and SV2C.

At present 13 isoforms pertaining to the family of synaptotagmins are known. All are characterised by two carboxyl-terminal $Ca^{2+}$ binding C2-domains, a central transmembrane domain (TMD), which anchors the synaptotagmin in the synaptic vesicle membrane, and an amino terminus having different lengths. After the $Ca^{2+}$ inflow the fusion of the synaptic vesicle with the plasma membrane is initiated, whereupon the intraluminal amino terminus of the synaptotagmin is presented extracellularly and is available as receptor anchor for BoNT/B and G. Analogously thereto, the fourth luminal domain of the SV2 isoforms is available extracellularly, after exocytosis, for the interaction with BoNT/A.

The character of individual amino acids of the binding pocket was so modified by specific mutagenesis that binding to a protein receptor is rendered more difficult or is inhibited. For this purpose, the $H_C$-fragments of BoNT/B and BoNT/G were expressed in E. coli and isolated in the postulated binding pocket in recombinant form as wild type or with individual amino acid substitutions (mutations/substitutions). For a GST-pull-down-assay, in order to study the interaction in vitro between BoNT/B and BoNT/G as well as between synaptotagmin I and synaptotagmin II, the respective GST-synaptotagmin-fusion protein was incubated with different quantities of the respective $H_C$-fragment of BoNT/B or, respectively, BoNT/G and a phase separation was performed. Free $H_C$-fragment remained in the separated supernatant while bound BoNT $H_C$-fragment could be detected in the solid phase, together with GST-synaptotagmin-fusion protein. Substitution of the respective $H_C$-fragments by the full-length BoNT/B and G in the GST-pull-down assay showed the same results.

Figure 1:
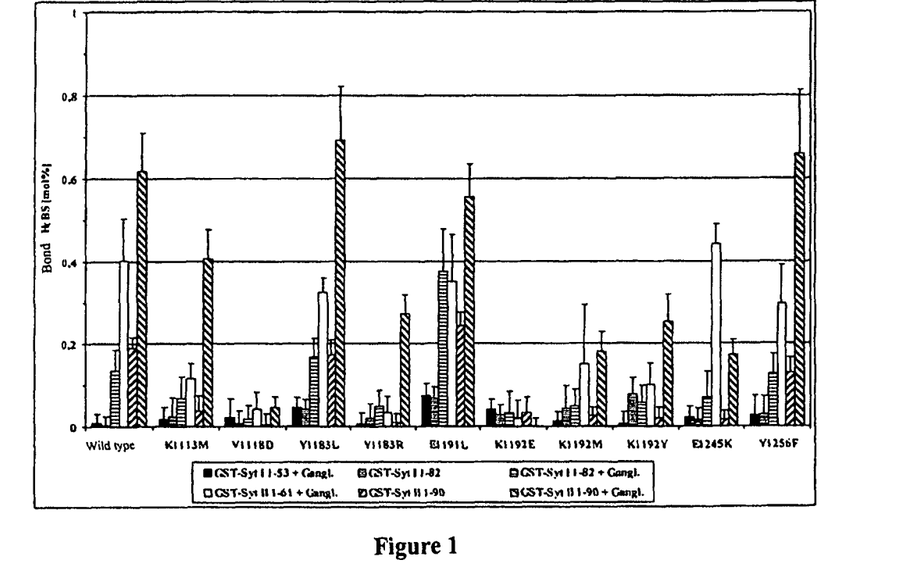
FIG. 1: Study of the in vitro bond of the wild type and mutated BoNT/B $H_C$-fragments to shortened GST-syt I and GST-syt II fusion proteins in the presence or absence of complex gangliosides by means of GST-pull-down assay.

It was found in this context that the BoNT/B wild type only binds in the presence of complex gangliosides and synaptotagmin I with transmembrane domain, while synaptotagmin II binds both with or without transmembrane domain as well as in the presence or absence of complex gangliosides. By specifically substituting amino acids within the protein receptor binding site of BoNT/B it was possible to significantly increase or decrease the interaction between both synaptotagmin molecules (FIG. 1).

Figure 2:
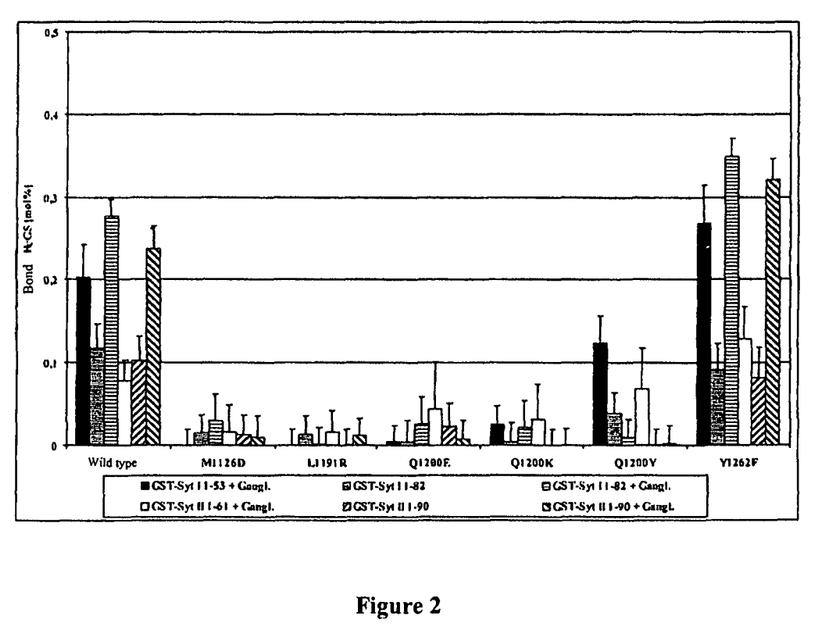
FIG. 2: Study of the in vitro bond of the wild type and mutated BoNT/G $H_C$-fragments to shortened GST-syt I and GST-syt II fusion proteins in the presence or absence of complex gangliosides by means of GST-pull-down assay.

Furthermore, it was shown for the BoNT/G wild type that binding to synaptotagmin I and synaptotagmin II, in each case with or without transmembrane domain, is taking place both in the presence as well as in the absence of complex gangliosides. By specifically substituting amino acids homologous to BoNT/B, within the protein receptor binding site of BoNT/G, it was possible to significantly increase or decrease the interaction between both synaptotagmin molecules (FIG. 2).

Figure 3:
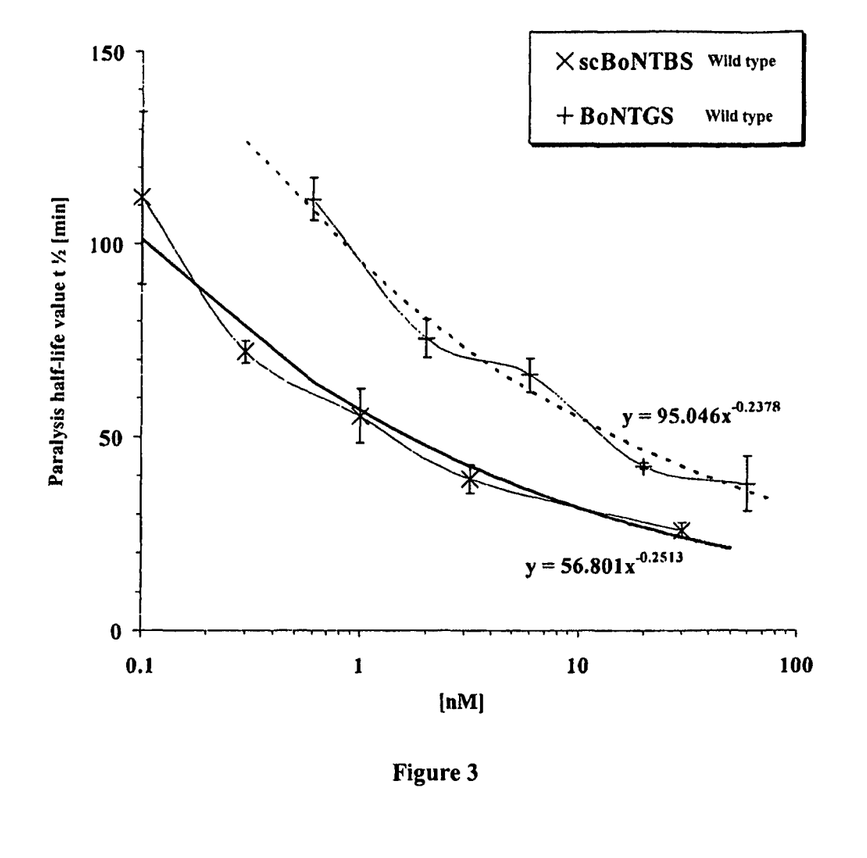
FIG. 3: Dosage-effect-graph of the BoNT/B and G wild types in the HDA. The applied potency functions permit a relative comparison of the paralysis times of single mutants with those of the associated wild types.
Figure 4:
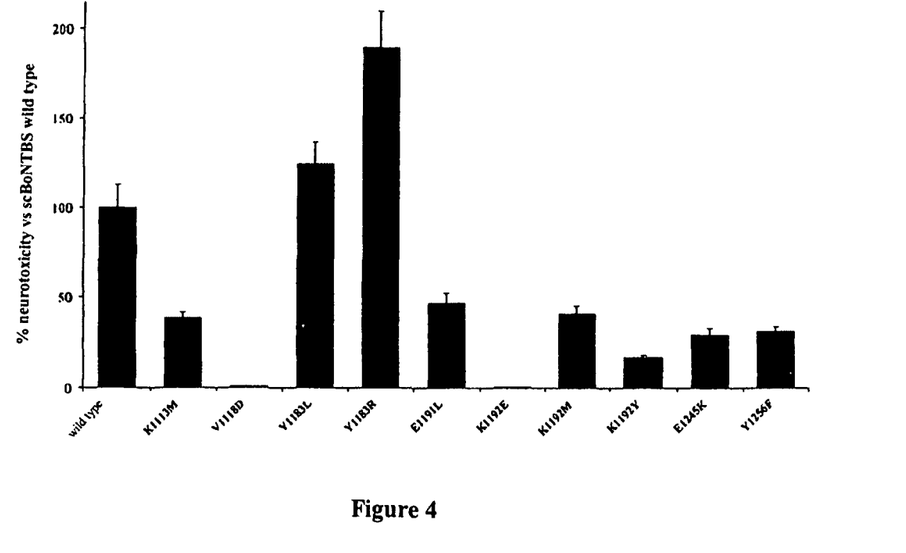
FIG. 4: Increase and decrease of the neurotoxicity of the BoNT/B single mutants compared to the wild type in the HDA.
Figure 5:
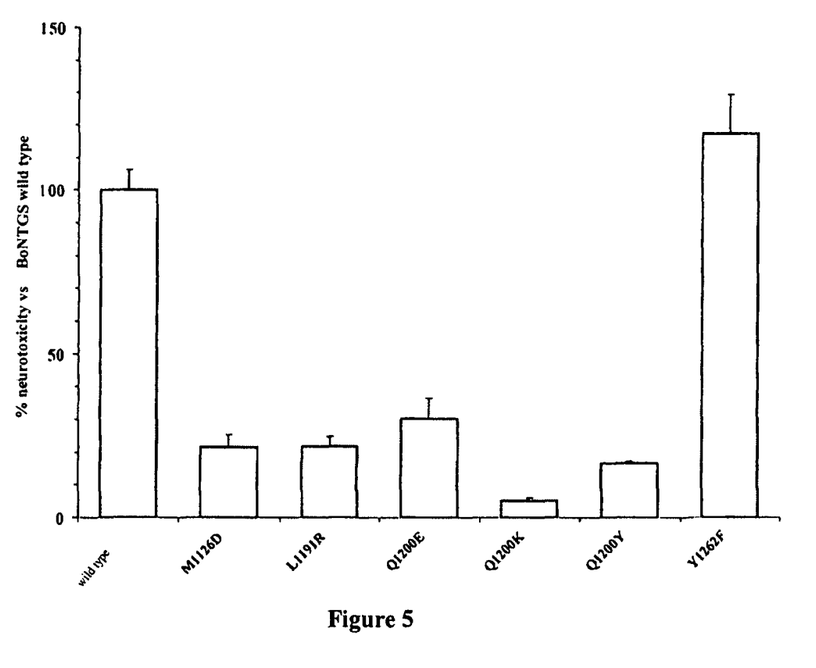
FIG. 5: Increase and decrease of the neurotoxicity of the BoNT/G single mutants compared to the wild type in the HDA.
Figure 6:
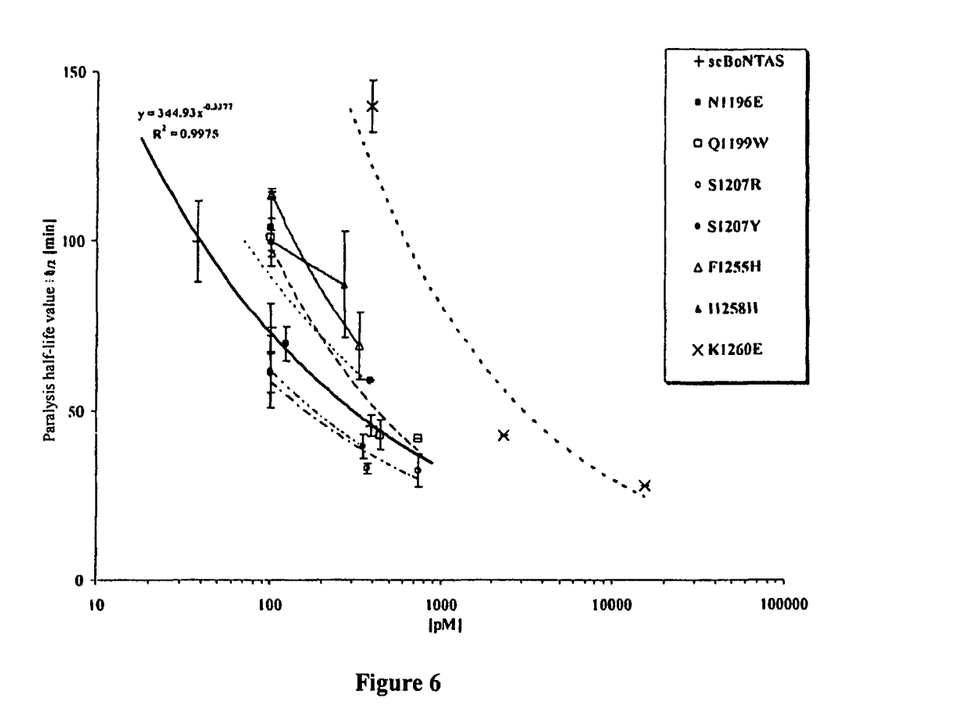
FIG. 6: Dosage-effect-graphs of the BoNT/A wild type and the BoNT/A single mutants in the HDA.

The potency of the full-length form of BoNT/A, B and G wild types was determined in the HDA by a dosage-effect-graph (FIGS. 3 and 6). The potency of the different full-length forms of BoNT/A, B and G single mutants was subsequently determined in the HDA (FIG. 6) and plotted against the potency of the BoNT/B and G wild types by means of an applied potency function (FIGS. 4 and 5). For example, the substitution of the amino acids valine 1118 by aspartate or lysine 1192 by glutamate in BoNT/B results in a drastic reduction of the potency to <2%. In contrast thereto, the mutation of the tyrosine 1183 in leucine or arginine, respectively, brings about a significant increase of the potency of BoNT/B (FIG. 4). Modifying tyrosine 1256 to phenylalanine in BoNT/G results likewise in an increase in potency while the mutation of glutamine 1200 in glutamate, lysine or tyrosine causes a considerable decrease of the potency of BoNT/G (FIG. 5). In the case of BoNT/A, modifying serine 1207 to arginine or tyrosine brings about an increase in potency while the mutation of lysine 1260 to glutamate causes a drastic potency reduction of the BoNT/A (FIG. 6).

According to a preferred embodiment the transport protein exhibits an affinity which is at least 15% higher or at least 15% lower than the native neurotoxin. Preferably, the transport protein exhibits an affinity which is at least 50% higher or lower, particularly preferred at least 80% higher or lower, and, in particular, at least 90% higher or lower than the native neurotoxin.

According to a preferred embodiment the modification of the HC takes place in the region of the $H_C$-fragment of the given neurotoxin. If the modification includes a substitution, deletion, insertion or addition, the latter may be performed, for example, by specific mutagenesis, methods in this context being known to the person skilled in the art. The amino acids present in the native neurotoxin are in this context modified either by naturally occurring or by not naturally occurring amino acids. Amino acids are, in principle, divided into different physicochemical groups. Aspartate and glutamate belong to the negatively-charged amino acids. Histidine, arginine and lysine belong to the positively-charged amino acids. Asparagine, glutamine, serine, threonine, cysteine and tyrosine belong to the polar amino acids. Glycine, alanine, valine, leucine, isoleucine, methionine, proline, phenylalanine and tryptophane belong to the non-polar amino acids. Aromatic side groups are to be found among the amino acids histidine, phenylalanine, tyrosine and tryptophane. In general, it is preferred to substitute an amino acid by a different amino acid pertaining to another physicochemical group.

According to a preferred embodiment of the invention, the transport protein is a Botulinus neurotoxin serotype A to G. The amino acid sequences of the native neurotoxins can in this context be obtained from publicly accessible databases as follows:

TABLE 1

Database numbers of the amino acid sequences and distribution of the sub-domains of the seven Botulinus neurotoxins.

| BoNT | Database no. of the protein sequence | Number of the amino acids | $H_N$ | HC $H_{CN}$ | $H_C$ $H_{CC}$ |
|---|---|---|---|---|---|
| BoNT/A | AAA23262 AAM75961 AAQ06331 BTCLAB | 1296 | 449-866 | 867-1091 | 1092-1296 |
|  | P10845 | 1296 | 449-866 | 867-1091 | 1092-1296 |
|  | CAA36289 | 1296 | 449-866 | 867-1091 | 1092-1296 |
|  | CAA51824 I40645 Q45894 | 1296 | 449-866 | 867-1091 | 1092-1296 |
| BoNT/B | AAL11499 AAL11498 | | | | |
|  | CAA73968 | 1291 | 442-855 | 866-1078 | 1079-1291 |
|  | AAK97132 | 1291 | 442-855 | 866-1078 | 1079-1291 |
|  | A48940 AAA23211 P10844 | 1291 | 442-855 | 866-1078 | 1079-1291 |
|  | BAC22064 | 1291 | 442-855 | 866-1078 | 1079-1291 |
|  | CAA50482 I40631 | 1291 | 442-855 | 866-1078 | 1079-1291 |

TABLE 1-continued

Database numbers of the amino acid sequences and distribution of the sub-domains of the seven Botulinus neurotoxins.

| BoNT | Database no. of the protein sequence | Number of the amino acids | $H_N$ | HC $H_{CN}$ | $H_C$ $H_{CC}$ |
|---|---|---|---|---|---|
| BoNT/C1 | A49777 BAA14235 BAB71749 CAA51313 S46431 | 1291 | 450-863 | 864-1092 | 1093-1291 |
|  | P18640 | 1291 | 450-863 | 864-1092 | 1093-1291 |
|  | BAA08418 | 1280 | 450-863 | 864-1083 | 1084-1280 |
|  | BAA89713 | 1280 | 450-863 | 864-1083 | 1084-1280 |
| BoNT/D | CAA38175 P19321 S11455 | 1276 | 446-859 | 860-1079 | 1080-1276 |
|  | AAB24244 | 1276 | 446-859 | 860-1079 | 1080-1276 |
|  | BAA07477 S70582 | 1285 | 446-859 | 860-1088 | 1089-1285 |
|  | BAA90661 | 1285 | 446-859 | 860-1088 | 1089-1285 |
| BoNT/E | BAB86845 CAA44558 S21178 | 1252 | 423-842 | 843-1066 | 1067-1252 |
|  | CAA43999 Q00496 | 1251 | 423-842 | 843-1066 | 1067-1251 |
|  | CAA43998 JH0256 P30995 | 1251 | 423-842 | 843-1066 | 1067-1251 |
| BoNT/F | 1904210A AAA23263 I40813 P30996 | 1274 | 440-860 | 861-1086 | 1087-1274 |
|  | CAA73972 | 1280 | 440-861 | 862-1087 | 1088-1280 |
|  | AAA23210 CAA57358 | 1278 | 440-861 | 862-1084 | 1085-1278 |
|  | CAA48329 S33411 | 1268 | 432-853 | 854-1075 | 1076-1268 |
| BoNT/G | CAA52275 Q60393 S39791 | 1297 | 447-860 | 861-1086 | 1087-1297 |

With regard to the $H_C$-fragment of these Botulinus neurotoxins, the amino acids in the amino acid positions from 867 to 1296 of the *C. botulinum* neurotoxin serotype A, 866 to 1291 of the *C. botulinum* neurotoxin serotype B, 864 to 1291 or, respectively, 1280 of the *C. botulinum* neurotoxin serotype C1, 860 to 1276 or, respectively, 1285 of the *C. botulinum* neurotoxin serotype D, 843 to 1251 or, respectively, 1252 of the *C. botulinum* or *C. butyricum* neurotoxin serotype E, 861 to 1274, 862 to 1280 or, respectively, 1278 and 854 to 1268 of the *C. botulinum* or, respectively, *C. baratii* neurotoxin serotype F 861 to 1297 of the *C. botulinum* neurotoxin serotype G are preferred for modification.

It is, therefore, preferred to modify post-translationally, and/or add, and/or delete, and/or insert, and/or substitute by an either naturally occurring or not naturally occurring amino acid at least one amino acid in the aforesaid positions.

According to a preferred embodiment, the neurotoxin is Botulinus neurotoxin serotype A. In this case, preferably at least one amino acid in the positions threonine 1195, asparagine 1196, glutamine 1199, lysine 1204, isoleucine 1205, leucine 1206, serine 1207, leucine 1209, aspartate 1213, leucine 1217, phenylalanine 1255, asparagine 1256, isoleucine 1258 and/or lysine 1260 of the Botulinus neurotoxin serotype A protein sequences is modified post-translationally, and/or added, and/or deleted, and/or inserted and/or substituted by an either naturally occurring or not naturally occurring amino acid. The positions asparagine 1196, glutamine 1199, serine 1207, phenylalanine 1255, isoleucine 1258 and/or lysine 1260 of the Botulinus neurotoxin serotype A protein sequences are particularly preferred. In particular, the positions serine 1207, substituted by arginine or tyrosine, and lysine 1260, substituted by glutamate, are preferred.

According to a preferred embodiment, the neurotoxin is Botulinus neurotoxin serotype B. In this case, preferably at least one amino acid in the positions lysine 1113, aspartate 1114, serine 1116, proline 1117, valine 1118, threonine 1182, tyrosine 1183, phenylalanine 1186, lysine 1188, glutamate 1191, lysine 1192, leucine 1193, phenylalanine 1194, phenylalanine 1204, phenylalanine 1243, glutamate 1245, lysine 1254, aspartate 1255 and tyrosine 1256 of the Botulinus neurotoxin serotype B protein sequences is modified post-translationally, and/or added, and/or deleted, and/or inserted and/or substituted by an either naturally occurring or not naturally occurring amino acid. The positions valine 1118, tyrosine 1183, glutamate 1191, lysine 1192, glutamate 1245 and tyrosine 1256 of the Botulinus neurotoxin serotype B protein sequences are particularly preferred. In particular, the positions of tyrosine 1183 and glutamate 1191, substituted by leucine, are preferred.

According to a further preferred embodiment, the neurotoxin is Botulinus neurotoxin serotype G. In this case, preferably at least one amino acid in the positions phenylalanine 1121, lysine 1123, alanine 1124, serine 1125, methionine 1126, valine 1190, leucine 1191, serine 1194, glutamate 1196, threonine 1199, glutamine 1200, leucine 1201, phenylalanine 1202, phenylalanine 1212, phenylalanine 1248, lysine 1250, aspartate 1251 and tyrosine 1262 of the Botulinus neurotoxin serotype G protein sequences is modified post-translationally, and/or added, and/or deleted, and/or inserted and/or substituted by an either naturally occurring or not naturally occurring amino acid. The positions methionine 1126, leucine 1191, threonine 1199, glutamine 1200, lysine 1250 and tyrosine 1262 of the Botulinus neurotoxin serotype G protein sequences are particularly preferred. In particular, the position tyrosine 1262, substituted by phenylalanine, is preferred.

The transport protein provided in the present invention exhibits an increased or reduced specific affinity of its protein-binding domain, in particular to molecules pertaining to the family of the synaptotagmins or the synaptic vesicle glycoproteins 2.

A further embodiment of the present invention relates to a composition containing a transport protein according to the invention and at least one intervening molecule (X). The intervening molecule may be a small organic molecule, a peptide or a protein; preferably covalently bonded to the transport protein by a peptide bond, an ester bond, an ether bond, a sulphide bond, a disulphide bond or a carbon-carbon-bond.

In addition, the intervening molecule includes all known therapeutically active substances. Cytostatics, antibiotics, virustatics, but also immunoglobulins are preferred in this context.

In a preferred embodiment, the protein is a protease, splitting one or a plurality of proteins of the release apparatus of neurotransmitters, the protease being selected from the group of neurotoxins consisting of the LCs of the *C. botulinum* neurotoxins, in particular of the serotype A, B, C1, D, E, F and G or a proteolytically active fragment of the LC of a *C. botulinum* neurotoxin, in particular a neurotoxin of the serotype A, B, C1, D, E, F and G, the fragment exhibiting at least 0.01%, preferably at least 5%, particularly preferably at least 50%, in particular at least 90% of the proteolytic activity of the native protease. Preferably, the transport protein and the protease are derived from the same *C. botulinum* neurotoxin serotype, in particular and preferably the $H_N$-domain of the transport protein and the protease are derived from the *C. botulinum* neurotoxin serotype A. The sequences of the proteases are generally accessible at databases and the database numbers are apparent from Table 1. The proteolytic activity of the proteases is determined by way of substrate separation kinetics (see Binz et al. (2002), Biochemistry 41(6), 1717-23).

According to a further embodiment of the present invention, a process for producing the transport protein is provided. In this case, in a first step a nucleic acid coding for the transport protein is provided. The coding nucleic acid may represent in this context RNA, DNA or mixtures thereof. The nucleic acid may furthermore be modified with regard to its nuclease resistance, such as e.g. by inserting phosphorthioate bonds. The nucleic acid may be produced from a starting nucleic acid, the latter being accessible e.g. by cloning from genomic or cDNA-databases. Moreover, the nucleic acid may be produced directly by solid phase synthesis. Suitable methods are known to the person skilled in the art. If one starts with a starting nucleic acid, a specific modification, e.g. by locality-specific mutagenesis, may be brought about, resulting in at least one addition, insertion, deletion and/or substitution on the amino acid level. The nucleic acid is then linked operatively to a suitable promoter. Suitable promoters for expression in known expression systems are known to the person skilled in the art. The choice of promoter depends in this case on the expression systems used for expression. In general, constitutive promoters are preferred, but inducible promoters may likewise be used. The construct produced in this manner includes at least one part of a vector, in particular regulatory elements, the vector being selected, for example, from λ-derivates, adenoviruses, baculoviruses, vaccinia viruses, SV40-viruses and retroviruses. The vector is preferably capable of expressing the nucleic acid in a given host cell.

The invention further provides host cells, which contain the vector and are suitable for expressing the vector. Numerous prokaryotic and eukaryotic expression systems are known in the state of the art, the host cells being selected, for example, from prokaryotic cells such as E. coli or *B. subtilis*, from eukaryotic cells such as *S. cerevisiae* and *P. pastoris*. Although higher eukaryotic cells, such as insect cells or mammal cells, may be used as well, host cells are nevertheless preferred, which, like *C. botulinum*, do not possess a glycosylation apparatus.

According to a preferred embodiment the nucleic acid codes for the $H_C$-fragment of the *C. botulinum* neurotoxin. This nucleic acid contains endonuclease-interfaces, flanking the nucleic acid coding for the $H_C$-fragment, the endonuclease sites being compatible with those of other $H_C$-fragments of *C. botulinum* neurotoxins, in order to permit their easy modular substitution in the gene coding for the transport protein, while the similarity of the amino acid sequence is preserved.

If a composition according to the invention is provided, which, apart from the transport system, further contains at least one intervening molecule, and this intervening molecule is a peptide or protein, functionalised either with a carboxyl-terminal cysteine or a mercapto-group, then, in an analogous manner, as described before, the peptide and/or protein may be produced recombinantly, for example by using binary vectors or various host cells. If the same host cell is used for the expression both of the transport protein and the peptide or protein, an intermolecular disulphide bond is preferably formed in situ. For a more efficient production in the same host cell, the nucleic acid coding for the peptide or protein may also be translated with that of the transport protein in the same reading frame, so that a single-chain polypeptide is produced. In this case, preferably an intramolecular disulphide bond is formed in situ. For simple hydrolysis of the likewise present peptide cross-linking between the transport protein and the peptide and/or protein, an amino acid sequence is inserted at the amino-terminus of the transport protein, which is either specifically recognised and split by the protease thrombin or by a specific endoprotease of the host cell.

Surprisingly, it was found that the insert-sequence CXXXZKTKSLVPRGSKBXXC (SEQ ID NO:1), with X signifying any desired amino acid and Z and B being selected independently of each other from alanine, valine, serine, threonine and glycine, is split efficiently in vivo by an endogenous protease of a bacterial host, preferably E. coli. The insertion of the insert-sequence between the amino acid sequence of the transport protein and a further peptide or protein therefore offers the advantage that post-treatment at a later stage, e.g. by thrombin, is not necessary. The E. coli-strain E. Coli K12 is particularly preferred.

Preferably, the insert-sequence forms part of a loop with 18 20, preferably amino acids.

If this is not possible, an appropriate intermolecular disulphide-bond, after separate purification of the transport protein and the protein, may subsequently be brought about by oxidation processes known to the person skilled in the art. The peptide or protein may also be obtained directly by synthesis or fragment condensation. Appropriate methods are known to the person skilled in the art.

The transport protein and the peptide, or protein, respectively, are subsequently purified. For this purpose methods are used, known to the person skilled in the art, such as e.g. chromatography-methods or electrophoresis.

A further embodiment of the present invention relates to the pharmaceutical composition, which includes the transport protein or a composition and optionally a pharmaceutically acceptable excipient, a diluent and/or an additive.

The pharmaceutical composition is suitable for oral, intravenous, subcutaneous, intramuscular and topical administration. Intramuscular administration is preferred in this context. A dosing unit of the pharmaceutical composition contains approximately 0.1 pg to 1 mg of transport protein and/or the composition according to the invention.

The pharmaceutical composition is suitable to treat disorders of neurotransmitter release and disorders such as hemifacial spasms, spasmodic torticollis, blepharospasm, spasticities, dystonias, migraine, pain, disorders of the neck and lumbar vertebral column, strabism, hypersalivation, wound healing, snoring and depression.

A further embodiment of the present invention includes a cosmetic composition, containing a transport protein and a cosmetically acceptable excipient, diluent and/or additive. The cosmetic composition is suitable for treating hyperhidrosis and facial wrinkles.

In detail, the present invention relates to a transport protein (Trapo), formed by modifying the HC of the neurotoxin produced by *C. botulinum*, preferably specifically binding to neurons, and preferably absorbed intracellularly by receptor-mediated endocytosis and translocated from the acid endosomal compartment into the cytosol of neurons. This protein is used as a transporting means in order to introduce into the cells proteases and other substances bound to the said transporting means, unable to penetrate physiologically into the plasma membrane and to reach the cytosol of nerve cells. The substrates of the proteases are intracellularly localised proteins and peptides participating in the transmitter release. After separation of the substrates, the specific functions of the neurons are blocked; the cells themselves are not damaged. One of these functions is exocytosis, bringing about the neurotransmitter release. If the release of transmitters is inhibited, the transmission of signals from cell to cell is blocked. For example, striated muscles are paralysed if the release of acetyl choline is inhibited at the neuromuscular contact point. This effect may be used therapeutically, if the transport protein is applied to nerve ends of spastic or dystonic muscles. Other active substances are, for example, substances exhibiting anti-viral action. Conjugated with the transport protein, they are of use for treating viral infections of the nervous system. The present invention also relates to the use of a transport protein for inhibiting the release of neurotransmitters.

Transport proteins with a relatively low affinity bind to the nerve cells, but are not absorbed by them. These transport proteins are therefore suitable to serve as specific transporting means towards the surface of the nerve cells.

If patients are treated with the progenitor toxins A and B from *C. botulinum*, the injection of these non-human proteins, despite the low dosage, causes the formation of antibodies, so that the therapy shows no effect and must therefore be stopped in order to prevent anaphylactic shock. By applying a substance with the same active mechanism having a higher transport efficiency of the enzymatic activity, the dosage may be lowered drastically and the formation of antibodies will not occur. These properties are attributed to the transport protein described herein.

Although examples for application are given, the suitable mode of application and the dosage is, in general, individually determined by the treating physician. Such decisions are routinely made by each physician well versed in the relevant special field. Thus, the mode of application and the dosage of the neurotoxin may e.g. be selected in accordance with the invention described herein, based on criteria such as the solubility of the selected neurotoxin or the intensity of the pain to be treated.

The treatment interval for the native progenitor toxins A and B from *C. botulinum* is currently three to four months on average. Prolonging this interval would reduce the risk of the formation of antibodies and allow a longer treatment period with BoNT. The increase of LC in the cytosol would retard its decomposition and would thus also prolong the duration of efficacy. The transport protein described here exhibits a higher affinity and absorption rate than the native HC.

The following example merely serves for elucidation and should not be understood in a limiting manner.

Material And Methods

Plasmid Construction and Preparation of Recombinant Proteins

Plasmids for E. coli expression of recombinant $H_C$-fragments of BoNT/B and BoNT/G as well as of the full-length form of BoNT/A, B and G with carboxyl-terminal StrepTag for affinity purification were brought about by PCR-methods with suitable primers, chromosomal DNA coding for BoNT/A (AAA23262) BoNT/B (AAA23211) and BoNT/G (CAA52275) and the expression vector pQe3 (Quiagen AG) serving as the starting vector. Shortened variations of rat-synaptotagmin I (syt I) (amino acids 1-53; amino acids 1-82) and rat-synaptotagmin II (syt II) (amino acids 1-61; amino acids 1-90) were cloned into the GST-coding vector pGEX-2T (Amersham Biosciences AB). The nucleic acid sequences of all plasmids were confirmed by DNA-sequencing. The recombinant $H_C$-fragments and those of the full-length form of BoNT were prepared at room temperature in the E. coli-strain M15 [pRep4] (Qiagen) during induction for ten hours and purified on a StrepTactin-matrix (IBA GmbH) in accordance with the manufacturer's instructions. The GST-fusion proteins obtained from E. coli BL21 were isolated with the aid of glutathione immobilised on sepharose micro-beads. Fractions containing the desired proteins were combined and dialysed against Tris-NaCl-triton-buffer (20 mM Tris-HCl, 150 mM NaCl, 0.5% Triton X-100, pH 7.2).

GST-Pull-Down Assay

GST-fusion proteins (0.12 nmol each), which had been immobilised on 10 µl GT-sepharose micro-beads, were incubated at 4° C. for 2 h with $H_C$-fragments (0.1 nmol) in the absence or in the presence of a bovine brain-ganglioside-mixture (18% GM1, 55% GD1a, 10% GT1b, 2% other gangliosides; Calbiochem; 20 pg each) in a total volume of 180 µl Tris-NaCl-triton-buffer. The micro-beads were collected by centrifuging, the supernatant was removed and the separated micro-beads were in each case rinsed three times with 400 µl of the same buffer. The rinsed pellet fractions were boiled in SDS-sample buffer and studied, together with the supernatant fractions, by SDS-PAGE and Coomassie blue staining.

The BoNT/B wild type binds only in the presence of complex gangliosides and synaptotagmin I with transmembrane domain, while synaptotagmin II binds with or without transmembrane domain as well as in the presence or in the absence of complex gangliosides. By specifically substituting amino acids within the protein receptor binding site of BoNT/B it was possible to significantly increase (E1191L; Y1183L) or decrease (V1118D; K1192E) the interaction between both synaptotagmin molecules (FIG. 1).

For the BoNT/G wild type it was shown that binding to synaptotagmin I and synaptotagmin II, in each case with or without transmembrane domain, is taking place both in the presence as well as in the absence of complex gangliosides. By specifically substituting amino acids homologous to BoNT/B, within the protein receptor binding site of BoNT/G, it was possible to significantly increase (Y1262F) or decrease (Q1200E) the interaction between both synaptotagmin molecules (FIG. 2).

By detecting the bond of the recombinant $H_C$-fragments of BoNT/B and G to isolated, immobilised gangliosides, it was possible to exclude damage to the function of the neighbouring ganglioside-binding pocket by the mutations introduced into the syt-binding pocket and to draw adequate conclusions to an intact tertiary structure of the $H_C$-fragment. These results were supported by CD-spectroscopic studies as well as by thermal denaturation experiments, likewise displaying intact tertiary structures of the mutated $H_C$-fragments of BoNT/B and G.

Mouse Hemidiaphragm Assay (HDA)

The neurotoxicity of the BoNT/A, B and G-mutants was determined as described by Habermann et al., Naunyn Schmiedeberg's Arch. Pharmacol. 311 (1980), 33-40.

The potency of the full-length form of BoNT/A, B and G wild types was determined in the HDA by a dosage-effect-graph (FIGS. 3 and 6). The potency of the different full-length forms of BoNT/A, B and G single mutants was subsequently determined in the HDA (FIG. 6) and plotted against the potency of the BoNT/B and G wild types by means of an applied potency function (FIGS. 4 and 5). Thus, the substitution of the amino acids valine 1118 by aspartate or lysine 1192 by glutamate in BoNT/B results in a drastic reduction of the potency to <2%. In contrast thereto, the mutation of the tyrosine 1183 in leucine or arginine, respectively, brings about a significant increase of the potency of BoNT/B (FIG. 4). Modifying tyrosine 1256 to phenylalanine in BoNT/G results likewise in an increase in potency while the mutation of glutamine 1200 in glutamate, lysine or tyrosine causes a considerable decrease of the potency of BoNT/G (FIG. 5). In the case of BoNT/A, modifying serine 1207 to arginine or tyrosine brings about an increase in potency while the mutation of lysine 1260 to glutamate causes a drastic potency reduction of the BoNT/A (FIG. 6).

The invention claimed is:

1. A transport protein, comprising a modified heavy chain of a *Clostridium botulinum* serotype B neurotoxin, wherein at least one amino acid in the positions valine 1118, tyrosine 1183, glutamate 1191, lysine 1192, glutamate 1245, and/or tyrosine 1256 of said heavy chain of the *Clostridium botulinum* serotype B neurotoxin is substituted by a naturally occurring amino acid, and wherein
the transport protein binds to the protein receptor of nerve cells with at least 15% higher or at least 15% lower affinity than a *Clostridium botulinum* serotype B native neurotoxin carboxy heavy chain.

2. The transport protein according to claim 1, wherein the transport protein binds to synaptotagmin I or II.

3. The transport protein according to claim 1, wherein the amino acid tyrosine is substituted in position 1183 by leucine.

4. The transport protein according to claim 1, wherein the amino acid glutamate is substituted in position 1191 by leucine.

5. A composition comprising the transport protein according to claim 1, further comprising an organic molecule, a peptide, or a protein, wherein said organic molecule, peptide, or protein is covalently bonded to the transport protein by a peptide bond, an ester bond, an ether bond, a sulphide bond, a disulphide bond or a carbon-carbon-bond, or wherein the protein and the transport protein are bonded covalently by an amino acid sequence.

6. The composition according to claim 5, wherein the organic molecule is a virustatic, cytostatic, antibiotic or an immunoglobulin.

7. The composition according to claim 5, wherein the protein is a protease.

8. The composition according to claim 7, wherein the protease includes one or a plurality of light chains (LCs) of serotypes A, B, Cl, D, E, F and/or G of the *Clostridium botulinum*, neurotoxin.

9. The composition according to claim 7, wherein the protease contains a protcolytically active fragment, derived from the light chain (LC) of a *Clostridium botulinum* neurotoxin selected from the group consisting of: the serotypes A, B, Cl, D, E, F and/or G of the *Clostridium botulinum* neurotoxin, and characterised in that it exhibits at least 0.01% of the proteolytic activity of the LC.

10. The composition according to claim 7, wherein the protease specifically splits defined substrates within the cholinergic motor neurons.

11. The composition according to claim 10, wherein the substrates are selected from proteins which are involved in the release of neurotransmitters in nerve cells and proteins which are capable of catalytic reactions within the nerve cell.

12. The composition according to claim 7 wherein the amino acid sequence that covalently bonds the transport protein and the protease is specifically recognized and split by an endopeptidase.

13. The composition according to claim 12, wherein the amino acid sequence includes the sequence CXXXZKTKSLVPRGSKBXXC (SEQ ID NO:1), X being any desired amino acid and Z and B being selected independently of one another from alanine, valine, serine, threonine and glycine.

14. The composition according to claim 12, wherein the protease and the transport protein are additionally bonded covalently by a disulphide bond; and
wherein, after splitting by the endopeptidase, the disulphide bond interlinks the protease and the transport protein, which, in turn, results in the formation of an active dual-chain protease.

15. A pharmaceutical composition containing the transport protein according to claim 1 as well as a pharmaceutically acceptable excipient, diluent and/or additive.

16. A method for treating a subject with a disorder or a disease for which a therapy with Botulinus neurotoxin is indicated, said method comprising administering to the subject an effective amount of pharmaceutical composition according to claim 15.

17. The method according to claim 16, wherein the disorder and the disease are selected from the group consisting of: hemi-facial spasm, spasmodic torticollis, blepharospasm, spasticities, dystonias, migraine, pain, disorders of the neck and lumbar vertebral column, strabism, hypersalivation, snoring, wound healing, and depressive disorders.

18. A cosmetic composition containing the transport protein according to claim 1 as well as, a cosmetically acceptable excipient, diluent and/or additive.

19. A method for treating the cosmetic indications hyperhidrosis and facial wrinkles, said method comprising administration of an effective amount of the cosmetic composition according to claim 18.

20. The transport protein of claim 1, wherein at least one amino acid in the positions valine 1118, tyrosine 1183, glutamate 1245, and/or tyrosine 1256 of the Botulinus neurotoxin serotype B protein sequences is substituted by a naturally occurring amino acid.

21. The transport protein according to claim 1, wherein the amino acid tyrosine is substituted in position 1183 by arginine.

* * * * *

UNITED STATES PATENT AND TRADEMARK OFFICE
CERTIFICATE OF CORRECTION

| | |
|---|---|
| PATENT NO. | : 8,481,040 B2 |
| APPLICATION NO. | : 11/919302 |
| DATED | : July 9, 2013 |
| INVENTOR(S) | : Andreas Rummel et al. |

It is certified that error appears in the above-identified patent and that said Letters Patent is hereby corrected as shown below:

On Title page 2, in the right hand column, replace

"Sycha, T., *et al.*, "Botulinum Toxin in the Treatment of Rare Head and Neck Pain Syndromes: A Systematic Review of the Literature," *J. Neurol.*, 251(1):Jan. 19-30, 2004"

with

--Sycha, T., *et al.*, "Botulinum Toxin in the Treatment of Rare Head and Neck Pain Syndromes: A Systematic Review of the Literature," *J. Neurol.*, 251(Suppl 1):I19-I30 (2004)--.

Signed and Sealed this
Eighth Day of October, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,481,040 B2 | Page 1 of 1 |
| APPLICATION NO. | : 11/919302 | |
| DATED | : July 9, 2013 | |
| INVENTOR(S) | : Rummel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1047 days.

Signed and Sealed this
Twenty-seventh Day of January, 2015

Michelle K. Lee
*Deputy Director of the United States Patent and Trademark Office*